(12) United States Patent
Kamal et al.

(10) Patent No.: US 9,150,840 B2
(45) Date of Patent: Oct. 6, 2015

(54) **ISOLATED BACTERIAL STRAIN OF *ACHROMOBACTER* SP. MTCC 5605 AND A HIGHLY ENANTIOSELECTIVE EPOXIDE HYDROLASE ISOLATED THEREFROM**

(75) Inventors: Ahmed Kamal, Hyderabad (IN); Rohini Khanna, Hyderabad (IN); Chityal Ganesh Kumar, Hyderabad (IN); Anver Basha Shaik, Hyderabad (IN); Matam Shiva Kumar, Hyderabad (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 16 days.

(21) Appl. No.: 14/000,730

(22) PCT Filed: Aug. 27, 2012

(86) PCT No.: PCT/IN2012/000569
§ 371 (c)(1),
(2), (4) Date: Aug. 21, 2013

(87) PCT Pub. No.: WO2013/030851
PCT Pub. Date: Mar. 7, 2013

(65) Prior Publication Data
US 2014/0011224 A1 Jan. 9, 2014

(30) Foreign Application Priority Data
Aug. 26, 2011 (IN) .......................... 2417/DEL/2011

(51) Int. Cl.
| | |
|---|---|
| *C12Q 1/34* | (2006.01) |
| *C12N 9/14* | (2006.01) |
| *C12R 1/025* | (2006.01) |
| *C12P 41/00* | (2006.01) |
| *C12P 7/18* | (2006.01) |

(52) U.S. Cl.
CPC ... *C12N 9/14* (2013.01); *C12P 7/18* (2013.01); *C12P 41/001* (2013.01); *C12R 1/025* (2013.01); *C12Y 303/02003* (2013.01)

(58) Field of Classification Search
None
See application file for complete search history.

(56) References Cited

U.S. PATENT DOCUMENTS

| | | | | |
|---|---|---|---|---|
| 3,957,579 | A * | 5/1976 | Sato et al. | 435/145 |
| 6,797,053 | B2 * | 9/2004 | Arnaut | 106/819 |
| 6,828,115 | B1 | 12/2004 | Zocher et al. | |

FOREIGN PATENT DOCUMENTS

| | | |
|---|---|---|
| WO | 2007043777 A1 | 4/2007 |
| WO | 2009008834 A1 | 1/2009 |

OTHER PUBLICATIONS

Database EMBL [Online], "*Achromobacter* sp. AKSH-4 partial 16S rRNA gene, isolate AKSH-4", Jan. 5, 2010.
G. D. Gojgic-Cvijovic, et al., "Biodegradation of petroleum sludge and petrolum polluted soil by a bacterial consortium: a laboratory study," Biodegradation, 23:1-14 (2012).
Dipti Sareen, et al., "Prospecting for efficient enantioselective epoxide hydrolases," Indian Journal of Biotechnology, 10:161-177 (Apr. 2011).
International Application for PCT/IN2012/000569 dated Jan. 10, 2013, 4 pages.

* cited by examiner

*Primary Examiner* — Kade Ariani
(74) *Attorney, Agent, or Firm* — Abelman, Frayne & Schwab

(57) ABSTRACT

The present invention relates to a novel epoxide hydrolase enzyme which aims to achieve a high degree of resolution towards a broader range of substrates with high enantioselectivity and yields with minimal product inhibition. The invention further relates to a new bacterial strain *Achromobacter* sp. MTCC 5605 isolated from a petroleum-contaminated sludge sample, capable of producing the said enzyme. It is notable that the enzyme can be used as whole bacterial cell preparation, which allows continuous hydrolysis of substrates at even higher concentration and have an advantage of being recycled. The invention further relates to a process for the hydrolysis of different aryl epoxides which are potential synthons of intermediates for the synthesis of chiral amino alcohols and bioactive compounds like β-blockers.

4 Claims, 9 Drawing Sheets

Scheme 1

Figure 1:
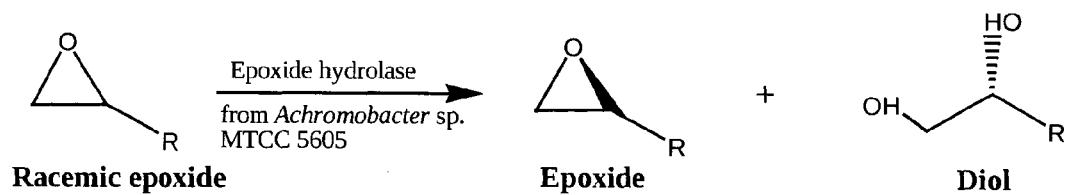
Figure 1:
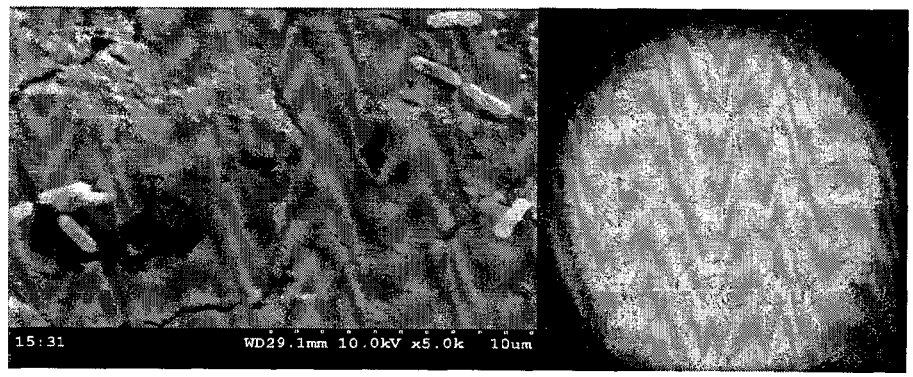

Reaction rate = 1.684 µmol / min; Enantiomeric ratio = 64. 09; Yield = 41.80 %

SEQUENCE LISTING

<160> NUMBER OF SEQ ID NOS: 1

<210> SEQ ID NO 1
<211> LENGTH: 798
<212> TYPE: DNA
<213> ORGANISM: Achromobacter sp. MTCC 5605

<400> SEQUENCE: 1

```
cgcgttacca agtgaatgcg tagatatggc ggaggaaaca ccgagtggcg aaggtcagcc      60
tccctggata aacacgacgc tcatgcacgg aaaagcgtgg ggacaaaaca ggatttagat     120
acccctggta gtccacgccc taaacgatgt caactagctg ttggggcctt cggggccttg     180
gtagcgcagc taacgcgtga agttgaccgc ctggggagta cggtcgcaag attaaaactc     240
aaaggaattg acggggaccc gtacaagcgg tggatgatgt ggattaattc gatgcaacgc     300
gaaaaacctt acctaccctt gacatgtctg gaatgccgaa gagatttggc agtgctcgca     360
agagaaccgg aacacaggtg ctgcatggct gtcgtcagct cgtgtcgtga gatgttgggt     420
taagtcccgc aacgagcgca acccttgtca ttagttgcaa cgaaagggca ctctaatgag     480
actgccggtg acaaaccgga ggaaggtggg gatgacgtca agtcctcatg gcccttatgg     540
gtagggcttc acacgtcata caatggtcgg gacagagggt cgccaacccg cgaggggag     600 ccaatcccag aaacccgatc gtagtccgga tcgcagtctg caactcgact gcgtgaactc     660
ggaatcgcta gtaatcgcgg atcagcatgt cgcggtgaat acgttcccgg gttttgtaca     720
caccgcccgt cacaccatgg gagtgggttt taccagaagt agttagccta actgccaggg     780
gggcgattac cacggtat                                                   798
```

ISOLATED BACTERIAL STRAIN OF *ACHROMOBACTER* SP. MTCC 5605 AND A HIGHLY ENANTIOSELECTIVE EPOXIDE HYDROLASE ISOLATED THEREFROM

RELATED APPLICATIONS

This application is a §371 of PCT/IN2012/000569 filed Aug. 27, 2012, and claims priority from Indian Patent Application No. 2417/DEL/2011 filed Aug. 26, 2011, both incorporated by reference in their entirety.

FIELD OF INVENTION

The present invention relates to a novel bacterial strain of *Achromobacter* sp. MTCC 5605 and a highly enantioselective epoxide hydrolase isolated therefrom. More particularly, the present invention relates to a novel epoxide hydrolase exhibiting high substrate tolerance, better substrate spectrum, non-toxic, easily and abundantly available whole cell biocatalyst for green and economic synthesis of enantio-enriched pharmaceutically important epoxides. The bacterial strain *Achromobacter* sp. MTCC 5605 has been isolated from petroleum contaminated sludge samples. The invention further relates to a process for the hydrolysis of different aryl epoxides which are potential synthons of intermediates for the synthesis of chiral amino alcohols and bioactive compounds like β-blockers.

BACKGROUND OF THE INVENTION AND DESCRIPTION OF PRIOR ART

Chirality is a key factor in the efficacy of many biomolecules which results in different stereoisomers having different biological activities. There is an increasing demand in the production of optically pure compounds due to regulatory requirements, prospects of lower toxicity and exquisite efficiency. Biocatalysis often referred to as a green chemistry approach, is widely researched and has developed into a standard technology for the production of enantiopure compounds. Enantiopure epoxides and diols are important chiral building blocks for pharmaceuticals and agrochemicals. A major challenge in the conventional organic synthesis is to generate optically active compounds with high enantiopurity and yield.

Several chemical procedures have been developed for the synthesis of optically active precursors like Sharpless-epoxidation with hydroperoxides and metal catalysts, which is limited to allylic alcohols [Katsuki, T. and Sharpless, K. B. (1980) *J. Am. Chem. Soc.* 102, 5975-5976]. Similarly, Jacobsen's asymmetric epoxidation using optically active (salen) manganese (III) complex is limited to steric and electronic nature of catalysts and prefers cis-alkenes [Jacobsen, E. N., Zhang, W., Muci, A. R., Ecker, J. R. and Deng, L. (1991) *J Am. Chem. Soc.* 113, 7063-7064]. The biological process includes direct stereoselective epoxidation of alkenes by monooxygenases [Archelas, A. and Furstoss, R. (1999) *Topics Curr. Chem.* 200, 159-191], and a two step synthesis using haloperoxidases and halohydrin epoxidase [Besse, P. and Veschambre, H. (1994) *Tetrahedron* 50, 8885-8927] or using other biocatalytic enzymes like and alcohol dehydrogenase and lipase [Cipiciani, A., Cittadini, M., and Fringuelli, F. (1998) *Tetrahedron* 54, 7883-7890]. However, lipase-mediated hydrolysis sometimes results in instability of the final product and further irreversibly denatures the enzyme. [Braun, B. and Klein, E. (1996) *Biotechnol. Bioeng.* 51: 327-341.] [Hasegawa, J., Ogura, M., Tsuda, S., Maemoto, S., Kutsuki, H. and Ohashi, T. (1990) *Agric. Biol. Chem.* 54, 1819-1827]. Many of these processes suffer from significant drawbacks like limited substrate scope, or efficient only at low concentrations, use of expensive and toxic metal catalysts, limited efficiency and productivity with varying degrees of enantioselectivities.

In the recent years, epoxide hydrolases have emerged as promising biocatalysts which offer a relatively simple route for the synthesis of optically enriched epoxides and diols under mild and eco-friendly conditions. This enzymatic resolution converts the inexpensive and easily available racemic mixture of aryl epoxides into optically active epoxides with excellent enantiomeric excesses. Aryl epoxides and the related compounds are potential intermediates for synthesis of chiral amino alcohols [Kamal, A., Chouhan, G. (2005) *Tetrahedron Asymmetry* 16, 2784-2789] and β-blockers [Kamal, A., Sandbhor, M., and Shaik, A. A. (2004) *Bioorg. Med. Chem. Lett.* 14, 4581-4583].

Epoxide hydrolase [EC 3.3.2.3] is a hydrolytic enzyme comprising of functionally related amino acid residues which catalyze the trans antiperiplanar addition of water to oxirane compound generating vicinal diol. The chiral substituted epoxides as well as the diols are valuable precursors in the downstream synthetic steps. Optically pure epoxides have gained attention as they are a common structural element in both simple and complex bioactive compounds and due to their electronic polarization and versatility of the oxirane function; they can be transformed into valuable synthons. Epoxide hydrolases are ubiquitous in nature and found in majority of organisms populating every branch of the evolutionary tree. They are found in majority of the mammals, plants and microbes. Mammalian epoxide hydrolases have been extensively studied. Inspite of its exceptionally high enantioselectivity for a large substrate spectrum, limited availability has hampered its large-scale production.

Microbial epoxide hydrolases have emerged as a new biotechnological tool for green synthesis of optically pure synthons. This environmentally compliant methodology is attractive as it minimizes the costs of resources and prevents the production of toxic waste in industrial applications. Over the past decade many epoxide hydrolases have been explored from microbial origin, but most of these enzymes have a limited substrate scope or rather act on low substrate concentrations due to low catalytic efficiency of the enzyme. Relatively better enantioselectivities were obtained from fungal epoxide hydrolases (Archelas et al. 1993; Nellaiah et al. 1996; Pedragosa 1997), but they have experimental constrains like inhibition at high substrate concentration, low enzymatic activity (Pedragosa et al. 1993). The mycelial and filamentous fungi are often characterized by high broth viscosity, nutrient concentrated zones, insufficient oxygen and mass transfer which reduces the productivity, high substrate concentrations cannot be usually used as they are inhibitory for the reaction and the reaction kinetics cannot be measured accurately as the insoluble substrates adsorb onto the mycelium, therefore the epoxide hydrolases require partially or purified enzymatic preparations for preparative scale experiments, however enzymatic preparations at higher substrate concentrations get deactivated or become less enantioselective at later stages (Morisseau et al. 1997 Liu et al. 2006).

Some of them have been cloned and functionally expressed to meet the growing demand via preparative scale application, for example, *Rhodotorula mucilaginosa* expressed in *Yarrowia lipolytica* [Labuschagne, M. and Albertyn, J. (2007) *Yeast* 24, 69-78]. Similarly, *Aspergillus niger* and *Rhodococcus erythropolis* expressed in *Escherichia coli* [Bottalla, A.-L., Ibrahim-Ouali, M., Santelli, M., Furstoss, R., and Archelas, A. (2007) *Adv. Syn. Catal.* 349, 1102-1110]. However, the substrate range of these enzymes in terms of their enantioselectivity has recently been examined. Higher enantioselectivity has been observed in limited number of organisms and only two organisms (*Aspergillus niger* and *Rhodococcus rhodochrous*) have so far been commercialized. Most of the known enzymes have limited substrate scope or rather act at low substrate concentrations due to low catalytic efficiency of the enzyme.

Majority of the epoxide hydrolases from various microbes reported to-date cannot tolerate high substrate concentrations and become less enantioselective during the biotransformation process. For example, in the case of *Sphingomonas* sp. HXN-200 the hydrolase can carry out the hydrolysis of styrene oxide at 320 mM, which yielded 40.2% with a final concentration of 128.6 mM of S-styrene oxide (S-enantiomer). And after 13.8 h the reaction velocity decreased and hydrolysis became less enantioselective. However, the epoxide hydrolase from *Achromobacter* sp. MTCC 5605 performs the hydrolysis of styrene oxide at 500 mM, which yielded 41.8% with a final concentration of 209 mM of S-styrene oxide. Further, the biotransformation process carried out by *Sphingomonas* sp uses a cell-free extract which required pre-processing involving the preparation of cell-free extract by passing the cells through French press, ultracentrifugation for cell debris removal followed by lyophilization of the cell-free extract which is cumbersome and cost-intensive, and the stability of the enzyme is less (only for 13.8 h). However, the present method using the epoxide hydrolases from *Achromobacter* sp. MTCC 5605 is cost-effective as there are no pre-processing steps involved, since it is a whole-cell biotransformation which allows continuous hydrolysis of epoxide substrates even at high concentrations and thereby the kinetic resolution process (biotransformation) can be prolonged for more than 48 h until the final chiral epoxide with high enantio-purity is obtained. Moreover, the lyophilized whole-cells can be stored for longer duration without any loss of activity and are abundantly available and accessible to the organic chemist.

The bacterial epoxide hydrolases reported in the prior art are referred to as below:
(1) *Bacillus megaterium* ECU1001 hydrolyses phenyl glycidylether which has an E value of 47.8 for a substrate concentration of 60 mM and yield of 25.6% [Tang, Y.-F., Xu, J.-H., Ye, Q. and Schulze, B. (2001) *J. Mol. Catal. B: Enzymatic* 13, 61-68].
(2) *Sphingomonas* HXN 200 hydrolyses styrene oxide at 320 mM concentration with an E value of 26-29 and yield of 40% [Liu, Z., Michel, J., Wang, Z., Wilholt, B. and Li, Z. (2006) *Tetrahedron: Asymmetry* 17, 47-52].

The usefulness of epoxide hydrolases as biocatalysts that produce enantioenriched epoxides is dependent on the factors like activity, availability, stability of the enzyme. The active whole cells can be used in lyophilized form for resolution of pharmaceutically important epoxides with high enantioselectivity. The interesting properties of this epoxide hydrolase has been justified further by exploring the biotransformation conditions like growth and epoxide hydrolase production, the ratio of substrate to biocatalyst concentration and the other physico-chemical properties like effect of temperature, pH, solvents, metal salts have been studied to increase the efficiency of the enzyme. In view of the non toxicity, easy availability and low cost, the whole cell catalysts i.e. bacterial epoxide hydrolases provide green and economical synthesis of optically pure synthons which can provide valuable methods for preparative scale applications.

In view of the above facts, there is an urgent need to provide a highly enantioselective epoxide hydrolase enzyme with a high catalytic efficiency and expanded substrate spectrum. It may be noted that a highly enantioselective bacterial epoxide hydrolase that belongs to the family Alcaligenaceae and genus *Achromobacter*, has not been previously documented. In majority of the bacterial epoxide hydrolases, it has been reported that they have low substrate tolerance, and limited substrate spectrum with low reaction rates, and therefore need further cloning or be functionally expressed to meet the growing demand for chiral biotransformations. The present invention fulfils these requirements as it provides a novel bacterial strain of *Achromobacter* sp. producing a novel epoxide hydrolase which functions even at high temperatures of up to 50 degree C. and pH of 9.0, which is a first report of its kind. Further, it is pertinent to mention here that whole cell resolutions allow continuous hydrolysis for high substrate concentrations; can be easily cultured, abundantly available and accessible to organic chemists. Therefore, there is an urge to develop a novel epoxide hydrolase for an efficient catalysis with expanded substrate spectrum and a cost effective process for practical applications. The present work fulfills these needs, focusing on the development of novel epoxide hydrolase as versatile biocatalyst. Epoxide hydrolase enzyme from the newly isolated bacterium *Achromobacter* sp. MTCC 5605 is much more enantioselective than any other known bacterial epoxide hydrolases

OBJECTIVES OF THE INVENTION

The main objective of the present invention is therefore to provide a novel bacterial strain of *Achromobacter* sp. MTCC 5605 and a highly enantioselective epoxide hydrolase isolated therefrom.

Another objective of the present invention is to provide a novel epoxide hydrolase enzyme which aims to achieve a high degree of resolution towards a broader range of substrates with high enantioselectivity and yields with minimal product inhibition.

Yet another objective of the present invention is to provide a novel enzyme from *Achromobacter* sp which is much more enantioselective (for high substrate concentration) as compared to other known bacterial epoxide hydrolases for the hydrolysis of different aryl epoxides which are potential synthons of intermediates for the synthesis of chiral amino alcohols and bioactive compounds like β-blockers.

Still another objective of the present invention is to provide a novel epoxide hydrolase from MTCC 5605, in the form of whole bacterial cells which allow continuous hydrolysis of substrates at even higher concentration and have an advantage of being recycled.

A further object of the present invention is to provide a method for producing the epoxide hydrolase enzyme comprising of various steps which include the enzyme enrichment under optimal conditions; whole cell kinetic resolution of epoxide substrates resulting in optically enriched epoxide and its recovery; examining the intrinsic regioselective properties of the enzyme like pH, temperature, and co-solvents, etc. which affect the kinetic rate of resolution.

Another object of the present invention is to provide a novel and simple route for enzyme isolation and purification.

SUMMARY OF THE INVENTION

The present invention provides a novel isolated bacterial strain of *Achromobacter* sp MTCC 5605 producing a novel epoxide hydrolase which catalyzes the enzymatic resolution of inexpensive and easily available racemic mixture of aryl epoxides into optically active epoxides with excellent enantiomeric excesses. The isolation of the said bacterial strain was done from a petroleum-contaminated sludge sample. *Achromobacter* sp. MTCC 5605 belongs to the family Alcaligenaceae, for which the epoxide hydrolase activity has not been previously reported.

In an embodiment, the present invention provides the isolation of a biologically pure culture of the microorganism *Achromobacter* sp. from a petroleum contaminated sludge sample which has been deposited in accordance with the Budapest Treaty on the International Recognition of the Deposit of Microorganisms at the Microbial Type Culture Collection & Gene Bank Institute of Microbial Technology, Sector 39-A, Chandigarh, -160036 India, under the accession number MTCC 5605. The deposit was made on Mar. 15, 2011, as Taxonomic designation *Achromobacter* sp., strain designation AKSH-4. The deposit was made for the purpose of Patent Procedure and all restrictions on the availability of the microorganism will be irrevocably removed upon the granting of a patent.

In yet another embodiment, the present invention provides a biologically pure culture, wherein the said culture produces a highly enantioselective epoxide hydrolase upon aerobic culturing in aqueous nutrient medium.

In yet another embodiment, the present invention provides a process for the resolution of epoxide racemic mixtures which comprises:

(a) incubating an enantiomeric mixture of epoxide along with the whole resting cells of *Achromobacter* sp. MTCC 5605 containing an active epoxide hydrolase at a temperature of 35 to 40 degree C. for 36 to 48 hours under stirring in a medium containing minimal carbon and nitrogen sources to obtain the conversion of racemic mixture;

(b) fractionating the racemic mixture of step (a) to obtain optically pure epoxide In still another embodiment, the present invention provides a process for the enrichment of enantioselective epoxide hydrolase enzyme which comprises:

growth of MTCC 5605 in the presence of epoxide substrate as a sole carbon source, Transfer of MTCC 5605 into the production medium containing optimal carbon and nitrogen sources In yet another embodiment, the present invention provides a process of preparing (S)-styrene oxide by selective hydrolysis of (R)-enantiomer with high enantiomeric ratio (E) and yield.

In still another embodiment of the present invention, the bioresolution of racemic styrene oxide with whole cells of MTCC 5605 in biphasic system preferentially hydrolyzed (R)-enantiomer of styrene oxide yielding (S)-enantiomer with >99% $ee_s$ (enantiomeric excess of the substrate). The substrate concentration could be increased up to 500 mM without affecting the $ee_s$ and (S)-styrene oxide was obtained with an optical purity of 100% and 41.8% yield (final concentration of 209 mM) and an enantiomeric ratio E=64.09 which is much robust than the previously reported native epoxide hydrolases In another embodiment, the present invention provides a biologically pure culture, wherein the aqueous nutrient medium used for culturing the same comprises assimiable sources of carbon, nitrogen and inorganic substances.

In still another embodiment, the present invention provides a process of optimization of different culture parameters for optimal production of epoxide hydrolase enzyme from MTCC 5605. In yet another embodiment, the present invention provides a process, wherein the epoxide hydrolase is highly enantioselective towards pharmaceutically important aryl epoxides like benzyl glycidyl ether, phenyl glycidyl ether, methoxyphenyl glycidyl ether, limonene epoxide, phenyl ethyl glycidate and indene oxide, which yields valuable synthons for chiral amino acids and β-blocker drugs.

In still another embodiment, the present invention provides a process wherein the whole cells of MTCC 5605 in biphasic system, hydrolysed R— enantiomer, yielding S— enantiomer with >99% $ee_s$ with an optical purity of 100% and 41.8% yield and an enantiomeric ratio E=64.09.

In a further embodiment, the present invention provides a process for the purification of epoxide hydrolase enzyme which is a rapid and simple method utilizing a pH gradient separation and purification protocol.

In another embodiment of the invention, the supernatant was separated after centrifugation of the MTCC 5605 whole cell homogenate mixture at pH 7 and the pellet was resuspended in buffer of pH 8.5, wherein the epoxide hydrolase activity was detected in the suspension. This suspension was centrifuged and the supernatant was fractionated on DEAE-cellulose column, equilibriated with Tris-HCl buffer of pH 8.5. The collected fractions with epoxide hydrolase activity were pooled, desalted by using Nanosep concentrators and separated using Amicon centrifugal concentrators.

In still another embodiment, present invention provides a process for the isolation of novel epoxide hydrolase from the bacterial strain of *Achromobacter* sp MTCC 5605 isolated from petroleum contaminated sludge sample comprising the steps of:

[a] isolating the bacterial strains by transferring 1.0 g of the sludge sample in 100 ml of enrichment medium comprising mineral salts medium with an epoxide as the sole carbon source and incubating at 35 to 40 degree C. for one week after which the isolates were purified for 2-3 times on nutrient agar plates;

[b] checking the purified isolates as obtained in step [a] for enantioselectivity and growth on fermentation medium for enzyme enrichment;

[c] selecting the strain *Achromobacter* sp. MTCC 5605 as the best producer of enantioselective epoxide hydrolase;

[d] purifying the epoxide hydrolase from *Achromobacter* sp. MTCC 5605 selected in step [c] after growing the strain in a fermentation medium with epoxide as the sole carbon source followed by homogenization;

[e] centrifuging the homogenate of step [d] at pH 7.0 and resuspending the pellet in Tris-HCl buffer of pH 8.5;

[f] centrifuging the suspension of step [e] to obtain the supernatant having the desired enanatioselctive epoxide hydrolase which was desalted by using Nanosep concentrators and separated using Amicon centrifugal concentrators.

BRIEF DESCRIPTION OF THE
ACCOMPANYING DRAWINGS

FIG. 1. Scanning electron microscope (SEM) and Gram-stained micrographs of *Achromobacter* sp. MTCC 5605, which is a Gram-negative, rod-shaped bacterium that does not produce pigment, on agar. Epoxide hydrolase enzyme from this newly isolated bacterium is much more enantioselective than any other known bacterial epoxide hydrolases. This highly enantioselective bacterial epoxide hydrolase belongs to the family Alcaligenaceae and genus *Achromobacter* which has not been previously documented either.

Figure 2:
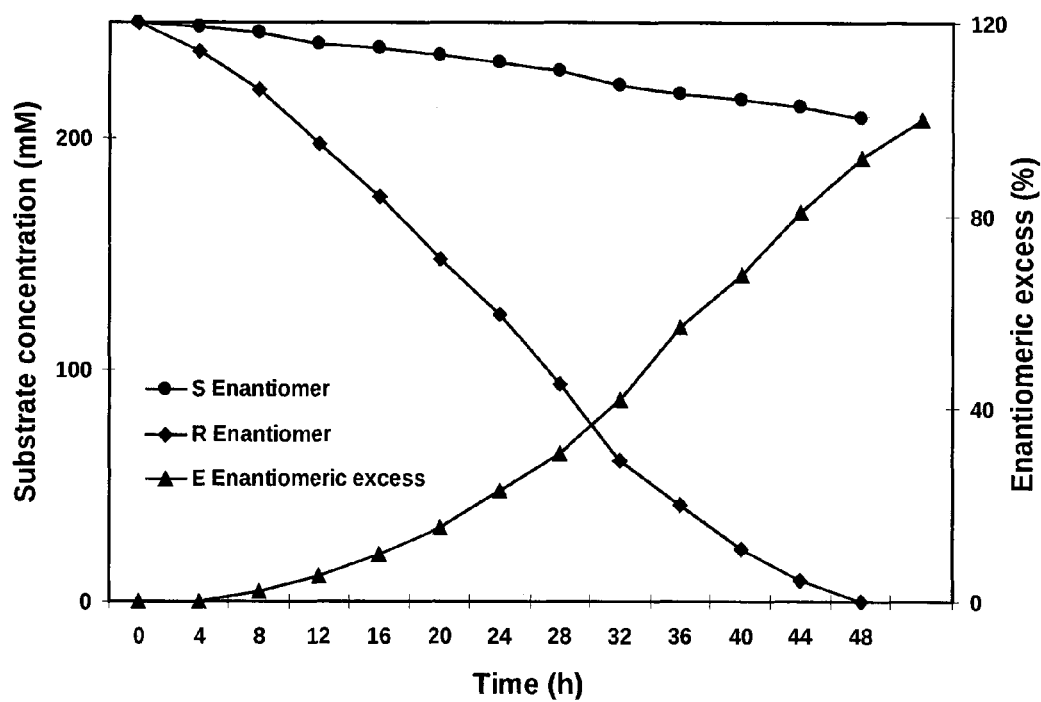

FIG. 2. Enantioselective hydrolysis of styrene oxide by epoxide hydrolase from *Achromobacter* sp. MTCC 5605. The bioresolution of racemic styrene oxide with whole cells in biphasic system preferentially hydrolyzed R-enantiomer of styrene oxide yielding S-enantiomer with >99% $ee_s$. The substrate concentration could be increased up to 500 mM without affecting the ee and (S) styrene oxide could be obtained with an optical purity of 100% and 41.8% yield and an enantiomeric ratio E=64.09 which is much robust than the previously reported epoxide hydrolases.

Figure 3:
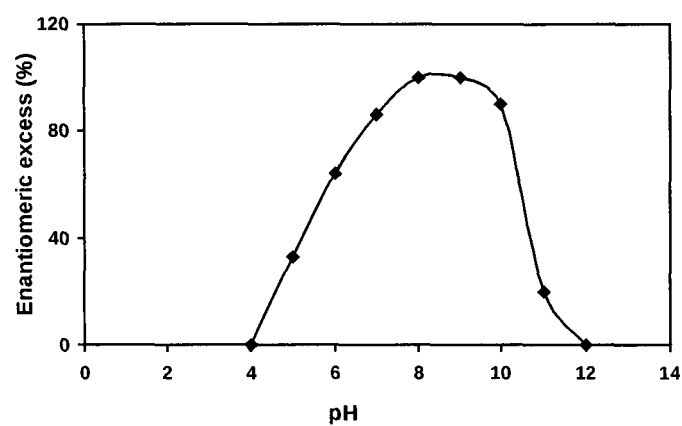

FIG. 3. Effect of pH on hydrolysis of styrene oxide by epoxide hydrolase from *Achromobacter* sp. MTCC 5605. Epoxide hydrolase from *Achromobacter* sp. MTCC 5605 hydrolysed styrene oxide under a relatively broader pH range as compared to the earlier reported enzyme, and the maximum activity was observed under alkaline conditions.

Figure 4:
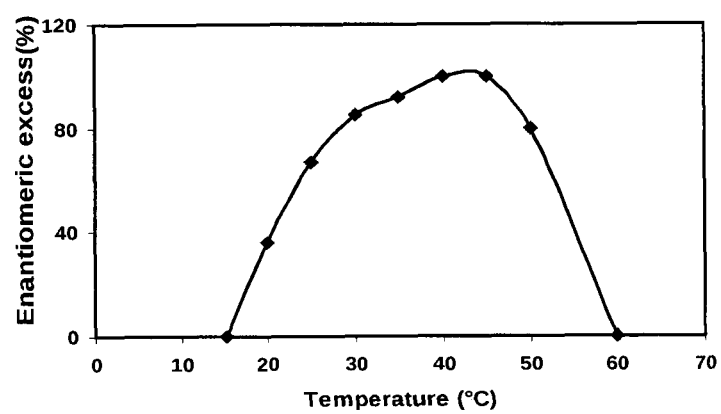

FIG. 4. Effect of temperature on hydrolysis of styrene oxide by epoxide hydrolase from *Achromobacter* sp. MTCC 5605. The temperature stability of epoxide hydrolase from *Achromobacter* sp. MTCC 5605 is 25-55° C. Maximum bioresolution was observed at 40-45° C. At temperatures over 55° C., rapid inactivation of the enzyme was observed. Most of the earlier reported enzymes were active between 28-35° C.

Figure 5:
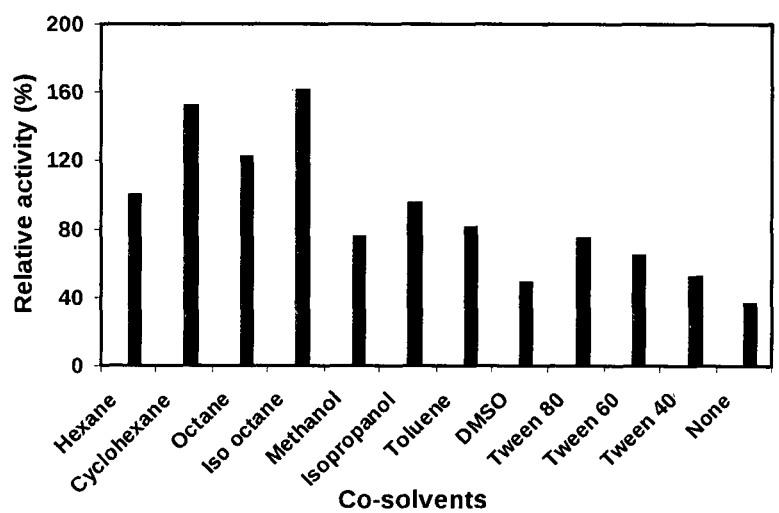

FIG. 5. Effect of co-solvents on hydrolysis of styrene oxide by epoxide hydrolase from *Achromobacter* sp. MTCC 5605. Most of the epoxides substrates have low solubility; hence addition of co-solvents was requisite for higher yields. A biphasic system of isooctane Tris-HCl yielded high enantiomeric ratio.

Figure 6:
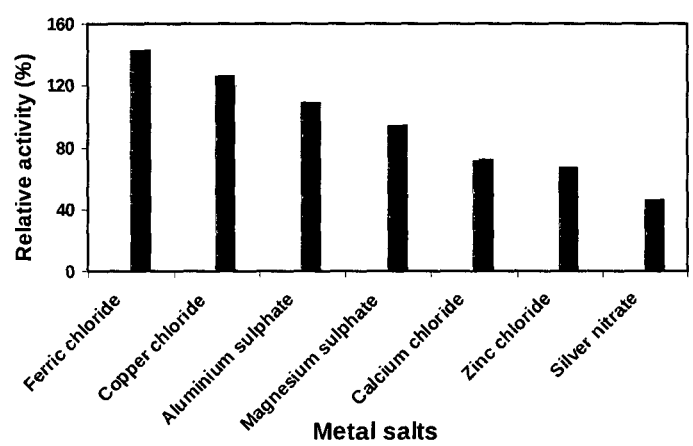

FIG. 6. Effect of metal salts on hydrolysis of styrene oxide by epoxide hydrolase from *Achromobacter* sp. MTCC 5605. Most epoxide hydrolases were not affected by metal salts, but the enzyme activity of epoxide hydrolase, from *Achromobacter* sp. MTCC 5605 varied with metal salts.

Figure 7:
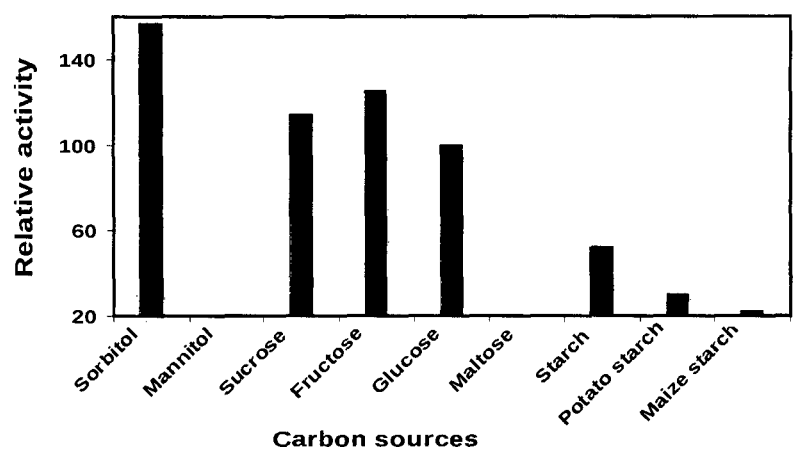

FIG. 7. Effect of carbon sources on hydrolysis of styrene oxide by epoxide hydrolase from *Achromobacter* sp. MTCC 5605. The enantioselectivity of the epoxide hydrolase enzyme was maximum when sorbitol was used as carbon source, followed by sucrose, glucose and fructose, however, starch-based carbon sources showed low or no enantioselectivity.

Figure 8:
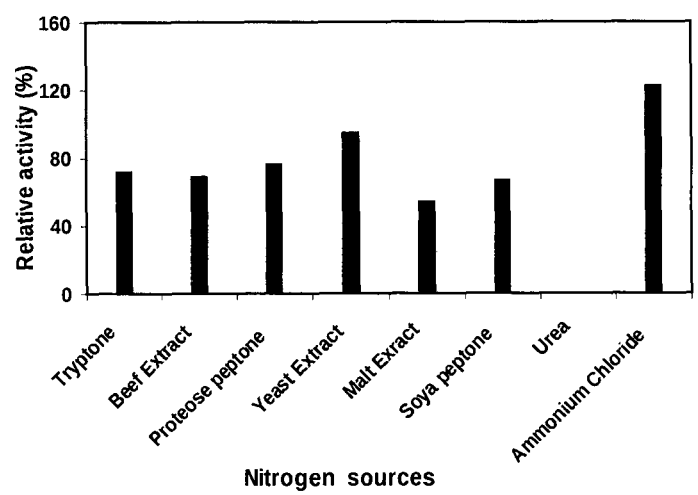

FIG. 8. Effect of nitrogen sources on hydrolysis of styrene oxide by epoxide hydrolase from *Achromobacter* sp. MTCC 5605. The enantioselectivity of the epoxide hydrolase enzyme was maximum when ammonium chloride was used as nitrogen source, followed by organic nitrogen sources. Other inorganic nitrogen sources showed no enzyme activity.

Figure 9:
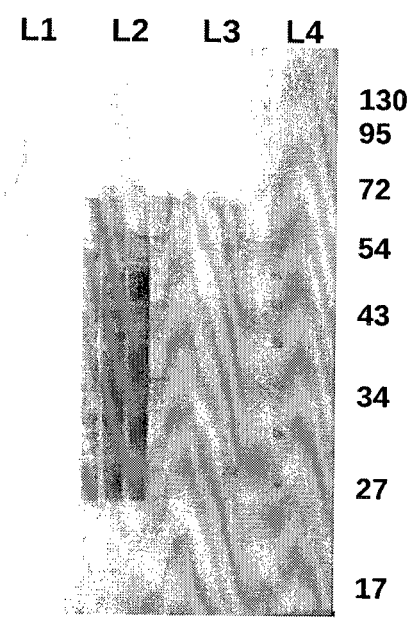

FIG. 9. SDS-PAGE of the purified epoxide hydrolase from *Achromobacter* sp. MTCC 5605. L1 and L3, Purified enzyme (95 kDa). L2, Enzyme eluted from DEAE cellulose column. L4, Molecular weight marker

DETAILED DESCRIPTION OF THE INVENTION

The present invention provides a novel epoxide hydrolase which is highly enantioselective even at high substrate concentrations as compared to other known bacterial epoxide hydrolases for the hydrolysis of different aryl epoxides which are potential synthons of intermediates for the synthesis of chiral amino alcohols and bioactive compounds like β-blockers. The novel epoxide hydrolase is prepared in the form of whole bacterial cells that are potent enough to carry out the reactions with high substrate concentration; thereby avoiding the use of lyophilized enzymatic preparations which are usually needed in case of fungal cultures, where the reactions with high activity are hampered due to fungal mycelia. These whole bacterial cells usually sequester the enzyme components in a small but concentrated form which is responsible for its high efficiency. The epoxide hydrolase enzyme of the present invention exhibits high enantiomeric ratio, hydrolyzing aryl epoxides at a very high substrate concentration, is superior in comparison with other known epoxide hydrolases in terms of high substrate tolerance, better substrate spectrum, non-toxic, easily and abundantly available whole cell biocatalyst for green and economic synthesis of enantio-enriched pharmaceutically important epoxides.

The novel epoxide hydrolase of the present invention is isolated from a novel isolated bacterial strain of *Achromobacter* sp MTCC 5605, which has been isolated from petroleum contaminated sludge samples collected from Petroleum Refinery Unit, Essar Oil Limited, Post Box No 24 Khambhalia, Vadinar 361305, District-Jamnagar, Gujarat, India.

Detailed Steps of Isolation of the Bacterial Strain

The bacterial colonies were subjected to two steps of screening: firstly the screening for epoxide hydrolase activity and secondly for enantioselectivity of the enzyme. The bacterial strains were isolated by transferring the sludge samples in enrichment medium, 1.0 g of each sludge sample in 100 ml of mineral salts medium for one week plated on agar plates with styrene epoxide as the sole carbon source and isolates were purified for 2-3 times on nutrient agar plates. The isolated pure organisms were scrapped off the agar plate and added to the microtubes individually containing fermentation medium and after two days the epoxide substrate dissolved in 0.5% cyclohexane was added. The bioconversion was carried out at 37° C. and 250 rpm for 24-48 h, then the reaction mixture was centrifuged, the supernatant was extracted with ethyl acetate and the enantiopurity of substrate was determined using GC.

The organism *Achromobacter* sp MTCC 5605 has been identified based on morphological, physiological and biochemical characterization and the 16s rDNA sequence determined has been deposited in EMBL database under the accession number FN645747.

The 16S rDNA sequence of *Achromobacter* sp. MTCC 5605 is:
cgcgttacca agtgaatgcg tagatatggc ggaggaaaca ccgagtggcg aaggtcagcc tccctggata aacacgacgc tcatgcacgg aaaagcgtgg ggacaaaaca ggatttagat acccctggta gtccacgccc taaacgatgt caactagctg ttgggggcctt cggggccttg gtagcgcagc taacgcgtga agttgac- cgc ctggggagta cggtcgcaag attaaaactc aaaggaattg acggggaccc gtacaagcgg tggatgatgt ggattaattc gatgcaacgc gaaaaaccttt acctaccctt gacatgtctg gaatgccgaa gagatttggc agtgctcgca agagaaccgg aacacaggtg ctgcatggct gtcgtcagct cgtgtcgtga gat- gttgggt taagtcccgc aacgagcgca acccttgtca ttagttgcaa cgaaagggca ctctaatgag actgccggtg acaaaccgga ggaaggtggg gatgacgtca agtcctcatg gcccttatgg gtagggcttc acacgtcata caatg- gtcgg gacagagggt cgccaacccg cgaggggag ccaatcccag aaac- ccgatc gtagtccgga tcgcagtctg caactcgact gcgtgaactc ggaatcgcta gtaatcgcgg atcagcatgt cgcggtgaat acgttcccgg gttttgtaca caccgcccgt cacaccatgg gagtgggttt taccagaagt agt- tagccta actgccaggg gggcgattac cacggtat The biologically pure culture of *Achromobacter* sp. MTCC 5605 produces the enzyme epoxide hydrolase upon aerobic cultivation in an aqueous nutrient medium preferably containing sources of carbon, nitrogen and inorganic substances. To enrich the enzyme, the organism was initially sub-cultured in mineral salt medium containing epoxide substrate as the sole carbon source at a temperature of 35 to 40 degree C. for 3 to 4 days. The mineral salt medium was adjusted to pH 8.0 with the following composition (per liter): ammonium sulphate 1 g, glucose, 5 g, $KH_2PO_4$ 3 g, $K_2HPO_4.3H_2O$ 6 g, NaCl 0.5 g, $MgSO_4.7H_2O$ 0.5 g, $CaCl_2$ 0.05 g and epoxide substrate 2.5 ml of 2% final concentration. After 3-4 days, the culture was transferred to a production medium (adjusted to pH 8.0) with following composition (per liter): glucose, 5 g, peptone 5 g, yeast extract 0.1 g, $KH_2PO_4$ 2 g, $K_2HPO_4.3H_2O$ 3 g and $MgSO_4.7H_2O$ 0.5 g. After two days the epoxide substrate dissolved in 0.5% cyclohexane was added and the biotransformation mixture was incubated at 35 degree C. The produced diol and the remaining unreacted epoxide were extracted with equal volume of ethyl acetate and quantified using Chiral GC and HPLC. The enantiomeric excess was calculated using equations cited in U.S. Patent No. 2010/0261251 A1 and U.S. Pat. No. 6,828,115. The enantiomeric ratio [E] of *Achromobacter* sp. MTCC 5605 was observed to be 64.09 with a yield of 41.8%. In the present process, the whole cells of MTCC 5605 in biphasic system, hydrolysed R— enantiomer, yielding S— enantiomer with >99% $ee_s$ with an optical purity of 100% and 41.8% yield and an enantiomeric ratio E=64.09.

EXAMPLES

The following examples are given by way of illustration and therefore should not be construed to limit the scope of the present invention.

Example 1

Isolation and Screening of Strains for Epoxide Hydrolase Activity

The bacterial strain producing epoxide hydrolase was isolated from petroleum contaminated sludge sample after preliminary screening steps and the enzyme activity was detected using the simple and standard representative of aryl epoxide, i.e., styrene oxide. The substrate was subjected to hydrolysis with whole bacterial cells in 0.1 M Tris buffer at pH 7.5. The reaction was monitored by observing the formation of the corresponding 1,2-diols by thin layer chromatography by comparison with synthesized diols and further confirmed using gas chromatography. The microorganism with high epoxide hydrolase activity was further identified as *Achromobacter* sp. MTCC 5605 (FIG. 1) based on its morphological, physiological and biochemical characterization (as given in Table 1) followed by 16S rDNA sequencing.

TABLE 1

Morphological, physiological and biochemical characteristics of *Achromobacter* sp. MTCC 5605

1) Morphological characteristics

| | | |
|---|---|---|
| a) | Gram staining | Gram-negative |
| b) | Shape | rods, clusters |
| c) | Size | moderate |
| d) | Motility | motile |
| e) | Colony shape | circular |
| f) | Colony margin | entire |
| g) | Colony surface | smooth |
| h) | Colony elevation | slightly convex |
| i) | Colony consistency | viscous |
| j) | Optical features | opaque |
| k) | Pigments | no pigment |
| l) | Endospore | terminal endospore |

Physiological characteristics
a) Growth in broth: Abundant
b) Oxygen requirement: Aerobic
c) Temperature range: 28-42° C.
d) pH range: 6.0-10.0
e) Salt tolerance: NaCl concentration tolerance up to 10%

Biochemical characteristics

| | | |
|---|---|---|
| a) | Indole test | negative |
| b) | Methyl red test | negative |
| c) | Vogues-Proskauer test | negative |
| d) | Simmon's citrate test | positive |
| e) | Nitrate reduction test | negative |
| f) | $H_2S$ production | positive |
| g) | Urease test | positive |
| h) | Catalase test | positive |
| i) | Oxidase test | negative |
| j) | Protease test | positive |
| k) | Amylase test | negative |
| l) | Gelatin hydrolysis | negative |
| m) | Gas production from glucose | negative |

Carbohydrate fermentation tests
Positive for glucose, fructose and sucrose, and
Negative for trehalose, maltose, lactose, mannose, arabinose, rhamnose, raffinose, melibiose, melizitose, sorbose, xylose, arabitol, sorbitol, dulcitol, inositol and mannitol Antibiotic sensitivity
Sensitive to Erythromycin (10 mcg), Gentamycin (10 mcg), Ciprofloxacin (5 mcg), Tetracycline (30 mcg), Chloramphenicol (30 mcg), Moxifloxacin (5 mcg) and Rifampicin (5 mcg)
Resistant to Penicillin-G (10 units), Methicillin (5 mcg), Amphotericin B and Nystatin.

TABLE 1 -continued

SEQUENCE LISTING of the 16S rDNA sequence of *Achromobacter* sp.
MTCC 5605

CSIR, IN
A novel bacterial strain of *Achromobacter* sp. MTCC 5605 and a
highly enantioselective epoxide hydrolase isolated therefrom
2417/DEL/2011
1
PatentIn version 3.5
1
798
DNA
*Achromobacter* sp. MTCC 5605
1

```
cgcgttacca agtgaatgcg tagatatggc ggaggaaaca ccgagtggcg aaggtcagcc   60
tccctggata aacacgacgc tcatgcacgg aaaagcgtgg ggacaaaaca ggatttagat  120
acccctggta gtccacgccc taaacgatgt caactagctg ttggggcctt cggggccttg  180
gtagcgcagc taacgcgtga agttgaccgc ctggggagta cggtcgcaag attaaaactc  240
aaaggaattg acggggaccc gtacaagcgg tggatgatgt ggattaattc gatgcaacgc  300
gaaaaacctt acctaccctt gacatgtctg gaatgccgaa gagatttggc agtgctcgca  360
agagaaccgg aacacaggtg ctgcatggct gtcgtcagct cgtgtcgtga gatgttgggt  420
taagtcccgc aacgagcgca accctttgtca ttagttgcaa cgaaagggca ctctaatgag  480
actgccggtg acaaaccgga ggaaggtggg gatgacgtca agtcctcatg gcccttatgg  540
gtagggcttc acacgtcata caatggtcgg gacagagggt cgccaacccg cgaggggag   600 ccaatcccag aaacccgatc gtagtccgga tcgcagtctg caactcgact gcgtgaactc  660
ggaatcgcta gtaatcgcgg atcagcatgt cgcggtgaat acgttcccgg gttttgtaca  720
caccgcccgt cacaccatgg gagtgggttt taccagaagt agttagccta actgccaggg  780
gggcgattac cacggtat                                                798
```

Example 2

Kinetic Resolution of Styrene Oxide Using Epoxide Hydrolase from *Achromobacter* sp. MTCC 5605

Whole cells of *Achromobacter* sp. MTCC 5605 at late log phase (resting cells) were added to 0.1 M Tris-HCl buffer at pH 8.0 containing styrene oxide (100 mM) and 0.5% cyclohexane and incubated at 40° C. at 250 rpm. The reaction was terminated by monitoring the complete selective degradation of one of the enantiomer. The remaining epoxide was recovered by extraction with equal volumes of ethyl acetate and the organic layer was dried over $Na_2SO_4$, filtered and vacuum concentrated. This concentrated sample was injected into the gas chromatograph (GC) to monitor the enantiomeric excess (FIG. 2). These promising results led to pursue further the biotransformation conditions to optimize the yield and enantioselectivity of the novel epoxide hydrolase. The present invention also provides the optimization of biotransformation conditions, such as culture medium, effect of different reaction conditions like pH and temperature, effect of co-solvents and metal salts.

Example 3

Effect of pH on Styrene Oxide Hydrolysis

Example 2 was repeated with different pH buffers. The epoxide hydrolase activity was detected from pH 7.0-10.0, moderate activity was observed between pH 6.0-7.0 and rapid decrease to no activity was observed under acidic conditions. The results (FIG. 3) suggested that the bioresolution by *Achromobacter* sp. MTCC 5605 was maximum under alkaline conditions.

Example 4

Effect of Temperature on Styrene Oxide Hydrolysis

Example 2 was repeated with varying temperatures ranging from 20-60° C. The temperature mainly influences the kinetic rate of reaction with maximum activity attained between 30-50° C.; however, temperatures lower than 30° C. resulted in slow hydrolysis and higher temperatures had no activity due to enzyme deactivation (FIG. 4).

Example 5

Effect of Co-Solvents on Styrene Oxide Hydrolysis

Example 2 was repeated with different co solvents. Most of the epoxide substrates have low solubility. Thus, to prevent auto-hydrolysis and low yield; it is obligatory to add a cosolvent. An organic-aqueous phase system of isooctane and Tris-HCl buffer resulted in high enantioselectivity and yield. Other co-solvents like cyclohexane, n-octane, iso-propanol and methanol also exhibited moderate to good activities, whereas toluene, Tween 80, Tween 60 showed intermediate activities, while DMSO, Tween-40, Tween-20 exhibited low enantioselectivity (FIG. 5).

Example 6

Effect of Metal Salts on Styrene Oxide Hydrolysis

Example 2 was repeated with different metal salts at 5 mM concentration under standard assay conditions. The enzyme activity increased in the presence of $FeCl_3$, $CuCl_2$, and $Al_2(SO_4)_3$, while there was almost no effect in the presence of $MgSO_4$; enzyme activity was partially inhibited by $CaCl_2$, and no enantioselectivity was observed with $BaCl_2$ and $MnSO_4$ (FIG. 6).

Example 7

Effect of Enzyme Inhibitors on Styrene Oxide Hydrolysis

Example 2 was repeated with different enzyme inhibitors (1 mM concentration) like 2-bromo-4'-methyl acetophenone, diethyl pyrocarbonate, dithiothreitol, phenyl hydrazine, hydroxylamine, sodium dodecyl sulphate, ethylenediaminetetraacetic acid, cetyltrimethylammonium bromide. However, none of them showed any inhibition of epoxide hydrolase activity.

Example 8

Effect of Carbon and Nitrogen Sources on Styrene Oxide Hydrolysis

The carbon and nitrogen sources are crucial for the growth and metabolic process of the microorganism. The growth and enzyme activity of the microorganism were largely affected by changing the carbon and nitrogen sources, with the prime goal of increasing the enzymatic level to obtain an efficient biocatalyst. The highest activity was observed when sorbitol was supplemented as carbon source followed by sucrose, glucose and fructose. Very low enantioselectivity was observed with starch-based carbon sources and no enantioselectivity was observed for mannitol and maltose substrates (FIG. 7). The organic nitrogen sources like tryptone, beef extract, malt extract and soya peptone favoured cell growth but not enzyme activity, while the inorganic nitrogen source, ammonium chloride, showed the highest epoxide hydrolase activity (FIG. 8). There was no activity observed with other inorganic nitrogen sources like urea and sodium nitrate.

Example 9

Hydrolysis with Different Pharmaceutically Important Substrates

This novel enzyme according to the invention can advantageously be explored for the hydrolysis of epoxide rings found in substrates of benzyl glycidyl ether, phenyl glycidyl ether, methoxyphenyl glycidyl ether, limonene epoxide, phenyl ethyl glycidate and indene oxide (Table 2), most of which are valuable intermediates for the synthesis of β-blocker drugs.

TABLE 2

Enantioselective hydrolysis of various pharmaceutically important epoxides

| S. No. | Substrate | Concentration (M) | Residual epoxide | | Diol product | |
|---|---|---|---|---|---|---|
| | | | ee (%) | Absolute configuration | Yield (%) | ee (%) | Absolute configuration |
| 1 | Styrene oxide | 0.5 | >99 | (S) | 42 | 65 | (R) |
| 2 | Benzyl glycidyl ether | 0.1 | >99 | (R) | 42 | 39 | (S) |
| 3 | (+) Limonene epoxide | 0.1 | >90 | (1S, 2R, 4R) | 40 | 32 | (1R, 2R, 4R) |
| 4 | Indene oxide | 0.1 | >92 | (1S, 2R) | 36 | (ND)* | (ND)* |
| 5 | Phenyl glycidyl ether | 0.1 | >80 | (S) | 39 | 26 | (R) |
| 6 | 4-Methoxy phenyl glycidyl ether | 0.1 | >86 | (S) | 41 | 23 | (R) |
| 7 | Phenyl ethyl glycidate | 0.1 | >87 | (2S, 3R) | 37 | 52 | (2R, 3R) |

(ND)*—Not determined

Example 10

Purification of Epoxide Hydrolase from *Achromobacter* sp

The enzyme enriched cells (resting cells, about 14 g) were suspended in 70 ml of Tris buffer (50 mM Tris-HCl-5 mM EDTA-5% glycerol-50 mM NaCl, pH 7.0) and further disrupted in 2 cycles of 5 min each, with a gap of 1 mM in each cycle, using ultrasound (Branson Sonifier W 250, output 80 W) placed in an ice bath. The homogenate was centrifuged at 15,000 rpm for 30 minutes at 4° C. The supernatant (lysate 1) in which epoxide hydrolase activity was not detected, was separated out. The pellet was re-extracted with the same Tris buffer at pH 8.5 and centrifuged at 15,000 rpm for 30 minutes at 5° C. and in this fraction (lysate 2), epoxide hydrolase enzyme activity was detected which was applied on a DEAE-cellulose column previously equilibrated with Tris buffer (pH 8.5). After washing the bound proteins were eluted with a linear gradient of 100 mM-1 M NaCl in the same buffer. Fractions of 1 ml were collected. All the fractions were assayed for enzyme activity. The active fractions were pooled and desalted by using Nanosep concentrators and separated using Amicon concentrators (3 and 9 kDa MWCO) by centrifugation. Then the sample was run on SDS-PAGE to determine the molecular mass of the protein which was observed to 95 kDa (FIG. 9).

ADVANTAGES OF THE INVENTION

Epoxide hydrolases from *Achromobacter* sp. MTCC 5605 have remarkable advantages which offer a simple and green route for the synthesis of optically enriched epoxides. A major challenge in the conventional organic synthesis is to generate optically pure compounds with high enantiopurities and good yields. Several chemo or bio-catalytic procedures have been developed like Sharpless-epoxidation (Katsuki et al. 1980), Jacobsen's asymmetric epoxidation (Jacobsen et al. 1991), alkene epoxidation by monooxygenases (Archelas and Furstoss 2001), two step synthesis using haloperoxidases and halohydrin epoxidase (Besse and Veschambre 1994) using lipase (Cipiciani et al. 1998) and alcohol dehydrogenase (Hasegawa et al. 1990). These processes were significantly affected because of limited substrate scope and use of expensive and toxic metal catalysts, limited efficiency and productivity and compliance with the stringent economical and environmental standards.

Many epoxide hydrolases have been explored earlier from microbial origin, but most of these enzymes have a limited substrate scope or rather act on low substrate concentrations due to low catalytic efficiency of the enzyme. This environmentally compliant methodology is attractive as it minimizes the costs of resources and prevents the production of toxic waste in industrial applications.

Although relatively better enantioselectivities were obtained from fungal epoxide hydrolases, but they have experimental constraints like inhibition at high substrate concentration and low enzymatic activity. The mycelial and filamentous fungi are often characterized by high broth viscosity, nutrient concentrated zones, insufficient oxygen and mass transfer which reduces the productivity, therefore the epoxide hydrolases require partially or purified enzymatic preparations for preparative scale experiments, however, enzymatic preparations at higher substrate concentrations get deactivated or become less enantioselective at later stages, which are avoided with the advantages of the present invention.

In the present invention, the whole cell resolutions allow continuous hydrolysis for high substrate concentrations; can be easily cultured, abundantly available and accessible to organic chemists.

This novel epoxide hydrolase offers an efficient catalysis with expanded substrate spectrum and a cost effective process for practical application.

The epoxide hydrolase from the newly isolated bacterium *Achromobacter* sp. MTCC 5605 is much more enantioselective than any other known bacterial epoxide hydrolases. The active whole cells can be used in lyophilized form for resolution of pharmaceutically important epoxides with high enantioselectivity. The biphasic hydrolysis using lyophilized cells allows the use of high substrate concentration. In view of the non-toxicity, easy availability and low cost of the whole cell catalysts provides green and economical synthesis of optically pure synthons.

We claim:

1. An aqueous composition of an isolated enantioselective epoxide hydrolase from *Achromobacter* MTCC 5605 having a molecular weight of 95 KDa, said enantiomeric epoxide hydrolase being active in the pH range of 5 to 11 and at a temperature ranging from 30° to 50° C., exhibiting hydrolysis of racemic aryl epoxides with >99% ee$_s$ at a substrate concentration up to 500 mM, yielding up to 42% of 100% optically pure aryl epoxides with a final concentration of up to 209 mM wherein said composition is free of petroleum contamination sled' e.

2. The aqueous composition as claimed in claim 1, wherein the epoxide hydrolase is highly enantioselective towards pharmaceutically important aryl epoxides selected from the group consisting of styrene oxide, benzyl glycidyl ether, phenyl glycidyl ether, methoxyphenyl glycidyl ether, limonene epoxide, phenyl ethyl glycidate and indene oxide, which yields synthons for chiral amino acids and β-blocker drugs.

3. A process for the resolution of racemic aryl epoxides using the epoxide hydrolase composition as claimed in claim 1, comprising the steps of:
    (a) incubating an enantiomeric mixture of epoxide along with said composition at a temperature of 35° to 40° C. for 36 to 48 hours under stirring in a medium containing carbon and nitrogen sources to obtain the conversion of racemic mixture;
    (b) fractionating the racemic mixture of step (a) to obtain optically pure epoxide.

4. A process for the purification of epoxide hydrolase from the bacterial strain of *Achromobacter* sp MTCC 5605 isolated from petroleum contaminated sludge sample comprising the steps of:
    [a] isolating said bacterial strains by transferring 1.0 g of the sludge sample in 100 ml of enrichment medium comprising mineral salts medium with an epoxide as sole carbon source and incubating at 35° to 40° C. for one week to form an isolate after which the isolates was purified 2-3 times on nutrient agar plates;
    [b] checking the purified isolates as obtained in step [a] for enantioselectivity and growth on a fermentation medium for enzyme enrichment;
    [c] selecting the strain *Achromobacter* sp. MTCC 5605 as the best producer of enantioselective epoxide hydrolase;
    [d] purifying the epoxide hydrolase from *Achromobacter* sp. MTCC 5605 selected in step [c] after growing the strain in a fermentation medium with epoxide as the sole carbon source, followed by homogenization to form a homogenate;
    [e] centrifuging the homogenate of step [d] at pH 7.0 to form a pellet and resuspending the pellet in Tris-HCl buffer of pH 8.5 to form a suspension, and;
    [f] centrifuging the suspension of step [e] to obtain the supernatant having the desired enantioselective epoxide hydrolase, followed by desalting concentrating and separation using a centrifugal concentrators to further purify the epoxide hydrolase.

* * * * *